(12) United States Patent
Dewey et al.

(10) Patent No.: US 7,955,392 B2
(45) Date of Patent: Jun. 7, 2011

(54) INTERSPINOUS PROCESS DEVICES AND METHODS

(75) Inventors: Jonathan M. Dewey, Memphis, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 636 days.

(21) Appl. No.: 11/610,522

(22) Filed: Dec. 14, 2006

(65) Prior Publication Data

US 2008/0147190 A1 Jun. 19, 2008

(51) Int. Cl.
*A61F 2/44* (2006.01)
*A61B 17/70* (2006.01)
(52) U.S. Cl. .................................. 623/17.16; 606/248
(58) Field of Classification Search .... 623/17.11–17.16; 606/246–279; 411/345, 340, 344, 346; *A61B 17/70, A61B 17/88; F16B 21/00*
See application file for complete search history.

(56) References Cited

U.S. PATENT DOCUMENTS

| | | | |
|---|---|---|---|
| 624,969 A | 5/1899 | Peterson | |
| 1,153,797 A | 9/1915 | Kegreisz | |
| 1,516,347 A | 11/1924 | Pataky | |
| 1,870,942 A | 8/1932 | Beatty | |
| 2,077,804 A | 4/1937 | Morrison | |
| 2,248,054 A | 7/1941 | Becker | |
| 2,299,308 A | 10/1942 | Creighton | |
| 2,472,103 A | 6/1949 | Giesen | |
| 2,485,531 A * | 10/1949 | Dzus et al. ................ | 606/310 |
| 2,607,370 A | 8/1952 | Anderson | |
| 2,677,369 A | 5/1954 | Knowles | |
| 2,685,877 A | 8/1954 | Dobelle | |
| 3,065,659 A | 11/1962 | Eriksson et al. | |
| 3,108,595 A | 10/1963 | Overment | |
| 3,426,364 A | 2/1969 | Lumb | |
| 3,486,505 A | 12/1969 | Morrison | |
| 3,604,487 A | 9/1971 | Gilbert | |

(Continued)

FOREIGN PATENT DOCUMENTS

DE 2821678 A1 11/1979

(Continued)

OTHER PUBLICATIONS

Scientific American, Apr. 1936, pp. 178-181, "Bone Surgery With Machine Tools", Fred H. Albee, M.D., F.A.C.S.*

(Continued)

*Primary Examiner* — Pedro Philogene
(74) *Attorney, Agent, or Firm* — Coats and Bennett P.L.L.C.

(57) ABSTRACT

The present application is directed to devices and methods for spacing and/or positioning spinous processes of vertebral members. The device may include a first wing to position on a first lateral side of spinous processes and a second wing to position on a second lateral side of spinous processes. An intermediate member extends between the wings and fits within the interspinous space. The device may be selectively adjustable from a first orientation with the second wing received by the intermediate member. This first orientation may include a reduced sized to facilitate insertion of the device with a lateral approach into the interspinous space. The device may also be moved to a second orientation with the wing deployed from the intermediate member. The second orientation may provide for the second wing to be positioned on the second side of the spinous process opposite from the first wing. The intermediate member may be positioned within the interspinous space to retain a predetermined distraction height.

19 Claims, 7 Drawing Sheets

U.S. PATENT DOCUMENTS

| | | | |
|---|---|---|---|
| 3,648,691 A | 3/1972 | Lumb et al. | |
| 3,779,239 A | 12/1973 | Fischer et al. | |
| 3,927,597 A * | 12/1975 | Stults et al. | 411/341 |
| 4,011,602 A | 3/1977 | Rybicki et al. | |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,401,112 A | 8/1983 | Rezaian | |
| 4,499,636 A | 2/1985 | Tanaka | |
| 4,509,517 A | 4/1985 | Zibelin | |
| 4,519,100 A | 5/1985 | Wills et al. | |
| 4,553,273 A | 11/1985 | Wu | |
| 4,554,914 A | 11/1985 | Kapp et al. | |
| 4,557,259 A | 12/1985 | Wu | |
| 4,573,454 A | 3/1986 | Hoffman | |
| 4,592,341 A | 6/1986 | Omagari et al. | |
| 4,599,086 A | 7/1986 | Doty | |
| 4,604,995 A | 8/1986 | Stephens et al. | |
| 4,611,582 A * | 9/1986 | Duff | 606/258 |
| 4,632,101 A | 12/1986 | Freedland | |
| 4,636,217 A | 1/1987 | Ogilvie et al. | |
| 4,646,998 A | 3/1987 | Pate | |
| 4,657,550 A | 4/1987 | Daher | |
| 4,662,808 A | 5/1987 | Camilleri | |
| 4,686,970 A | 8/1987 | Dove et al. | |
| 4,704,057 A | 11/1987 | McSherry | |
| 4,721,103 A * | 1/1988 | Freedland | 606/319 |
| 4,759,769 A | 7/1988 | Hedman et al. | |
| 4,787,378 A | 11/1988 | Sodhi | |
| 4,822,226 A | 4/1989 | Kennedy | |
| 4,827,918 A | 5/1989 | Olerud | |
| 4,834,600 A | 5/1989 | Lemke | |
| 4,862,891 A | 9/1989 | Smith | |
| 4,863,476 A | 9/1989 | Shepperd | |
| 4,886,405 A | 12/1989 | Blomberg | |
| 4,892,545 A | 1/1990 | Day et al. | |
| 4,913,144 A | 4/1990 | Del Medico | |
| 4,931,055 A | 6/1990 | Bumpus et al. | |
| 4,932,975 A | 6/1990 | Main et al. | |
| 4,969,887 A | 11/1990 | Sodhi | |
| 4,997,432 A | 3/1991 | Keller | |
| 5,000,166 A | 3/1991 | Karpf | |
| 5,011,484 A | 4/1991 | Breard | |
| 5,047,055 A | 9/1991 | Bao et al. | |
| 5,059,193 A | 10/1991 | Kuslich | |
| 5,067,864 A * | 11/1991 | Dewey et al. | 411/344 |
| 5,092,866 A | 3/1992 | Breard et al. | |
| 5,097,820 A | 3/1992 | Shulman et al. | |
| 5,098,433 A | 3/1992 | Freedland | |
| 5,108,240 A * | 4/1992 | Liebig | 411/344 |
| 5,171,278 A | 12/1992 | Pisharodi | |
| 5,201,734 A | 4/1993 | Cozad et al. | |
| 5,267,999 A | 12/1993 | Olerud | |
| 5,290,312 A | 3/1994 | Kojimoto et al. | |
| 5,306,275 A | 4/1994 | Bryan | |
| 5,306,310 A | 4/1994 | Siebels | |
| 5,312,405 A | 5/1994 | Korotko et al. | |
| 5,360,430 A | 11/1994 | Lin | |
| 5,366,455 A | 11/1994 | Dove | |
| 5,370,697 A | 12/1994 | Baumgartner | |
| 5,390,683 A | 2/1995 | Pisharodi | |
| 5,395,370 A | 3/1995 | Muller et al. | |
| 5,401,269 A | 3/1995 | Buttner-Janz et al. | |
| 5,403,316 A | 4/1995 | Ashman | |
| 5,415,661 A | 5/1995 | Holmes | |
| 5,426,130 A * | 6/1995 | Thurber et al. | 522/14 |
| 5,437,672 A | 8/1995 | Alleyne | |
| 5,437,674 A | 8/1995 | Worcel et al. | |
| 5,439,463 A | 8/1995 | Lin | |
| 5,454,812 A | 10/1995 | Lin | |
| 5,458,641 A | 10/1995 | Ramirez Jimenez | |
| 5,480,442 A | 1/1996 | Bertagnoli | |
| 5,484,440 A | 1/1996 | Allard | |
| 5,489,307 A | 2/1996 | Kuslich et al. | |
| 5,496,318 A | 3/1996 | Howland et al. | |
| 5,518,498 A | 5/1996 | Lindenberg et al. | |
| 5,536,268 A | 7/1996 | Griss | |
| 5,545,170 A | 8/1996 | Hart | |
| 5,554,191 A | 9/1996 | Lahille et al. | |
| 5,562,662 A | 10/1996 | Brumfield et al. | |
| 5,562,735 A | 10/1996 | Margulies | |
| 5,571,192 A | 11/1996 | Schonhoffer | |
| 5,599,279 A | 2/1997 | Slotman et al. | |
| 5,609,634 A | 3/1997 | Voydeville | |
| 5,609,635 A | 3/1997 | Michelson | |
| 5,609,636 A | 3/1997 | Kohrs et al. | |
| 5,628,756 A | 5/1997 | Barker, Jr. et al. | |
| 5,630,816 A | 5/1997 | Kambin | |
| 5,645,599 A | 7/1997 | Samani | |
| 5,653,762 A | 8/1997 | Pisharodi | |
| 5,653,763 A | 8/1997 | Errico et al. | |
| 5,658,335 A | 8/1997 | Allen | |
| 5,662,657 A | 9/1997 | Carn | |
| 5,665,096 A | 9/1997 | Yoon | |
| 5,665,122 A | 9/1997 | Kambin | |
| 5,667,513 A | 9/1997 | Torrie et al. | |
| 5,674,295 A | 10/1997 | Ray et al. | |
| 5,676,702 A | 10/1997 | Ratron | |
| 5,683,464 A | 11/1997 | Wagner et al. | |
| 5,685,826 A | 11/1997 | Bonutti | |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,455 A | 12/1997 | Saggar | |
| 5,707,390 A | 1/1998 | Bonutti | |
| 5,716,416 A | 2/1998 | Lin | |
| 5,723,013 A | 3/1998 | Jeanson et al. | |
| 5,725,341 A | 3/1998 | Hofmeister | |
| 5,746,762 A | 5/1998 | Bass | |
| 5,755,797 A | 5/1998 | Baumgartner | |
| 5,772,661 A | 6/1998 | Michelson | |
| 5,792,085 A | 8/1998 | Walters | |
| 5,797,909 A | 8/1998 | Michelson | |
| 5,800,547 A | 9/1998 | Schafer et al. | |
| 5,800,549 A | 9/1998 | Bao et al. | |
| 5,810,815 A | 9/1998 | Morales | |
| 5,836,948 A | 11/1998 | Zucherman et al. | |
| 5,849,004 A | 12/1998 | Bramlet | |
| 5,860,977 A | 1/1999 | Zucherman et al. | |
| 5,888,196 A | 3/1999 | Bonutti | |
| 5,888,224 A | 3/1999 | Beckers et al. | |
| 5,893,890 A | 4/1999 | Pisharodi | |
| 5,941,881 A | 8/1999 | Barnes | |
| 5,976,186 A | 11/1999 | Bao et al. | |
| 5,980,523 A | 11/1999 | Jackson | |
| 6,022,376 A | 2/2000 | Assell et al. | |
| 6,042,582 A | 3/2000 | Ray | |
| 6,048,342 A | 4/2000 | Zucherman et al. | |
| 6,059,829 A | 5/2000 | Schlapfer et al. | |
| 6,068,630 A | 5/2000 | Zucherman et al. | |
| 6,083,225 A | 7/2000 | Winslow et al. | |
| 6,086,595 A | 7/2000 | Yonemura et al. | |
| 6,113,602 A | 9/2000 | Sand | |
| 6,125,479 A * | 10/2000 | Fraleigh | 4/252.1 |
| 6,126,689 A | 10/2000 | Brett | |
| 6,126,691 A | 10/2000 | Kasra et al. | |
| 6,127,597 A | 10/2000 | Beyar et al. | |
| 6,132,464 A | 10/2000 | Martin | |
| 6,139,549 A | 10/2000 | Keller | |
| 6,159,212 A | 12/2000 | Schoedinger, III et al. | |
| 6,171,339 B1 | 1/2001 | Houfburg et al. | |
| 6,174,311 B1 | 1/2001 | Branch et al. | |
| 6,190,413 B1 * | 2/2001 | Sutcliffe | 623/17.11 |
| 6,190,414 B1 | 2/2001 | Young | |
| 6,214,050 B1 | 4/2001 | Huene | |
| 6,224,607 B1 | 5/2001 | Michelson | |
| 6,224,631 B1 | 5/2001 | Kohrs | |
| 6,241,729 B1 | 6/2001 | Estes et al. | |
| 6,261,296 B1 | 7/2001 | Aebi et al. | |
| 6,261,586 B1 | 7/2001 | McKay | |
| 6,293,949 B1 | 9/2001 | Justis et al. | |
| 6,336,930 B1 | 1/2002 | Stalcup et al. | |
| 6,348,053 B1 | 2/2002 | Cachia | |
| 6,352,537 B1 | 3/2002 | Strnad | |
| 6,364,883 B1 | 4/2002 | Santilli | |

| | | | | | |
|---|---|---|---|---|---|
| 6,371,987 B1 | 4/2002 | Weiland et al. | 2004/0010316 A1 | 1/2004 | William et al. |
| 6,375,682 B1 | 4/2002 | Fleischmann et al. | 2004/0059318 A1 | 3/2004 | Zhang et al. |
| 6,402,750 B1 | 6/2002 | Atkinson et al. | 2004/0087947 A1 | 5/2004 | Lim et al. |
| 6,402,751 B1 | 6/2002 | Hoeck et al. | 2004/0097931 A1 | 5/2004 | Mitchell |
| 6,419,704 B1 | 7/2002 | Ferree | 2004/0106927 A1 | 6/2004 | Ruffner et al. |
| 6,435,789 B2 * | 8/2002 | Gaudron ............. 411/344 | 2004/0133204 A1 | 7/2004 | Davies |
| 6,440,169 B1 | 8/2002 | Elberg et al. | 2004/0133280 A1 | 7/2004 | Trieu |
| 6,447,513 B1 | 9/2002 | Griggs | 2004/0138662 A1 | 7/2004 | Landry et al. |
| 6,451,019 B1 | 9/2002 | Zucherman et al. | 2004/0167625 A1 | 8/2004 | Beyar et al. |
| 6,500,178 B2 | 12/2002 | Zucherman et al. | 2004/0199255 A1 | 10/2004 | Mathieu et al. |
| 6,511,508 B1 | 1/2003 | Shahinpoor et al. | 2004/0249388 A1 | 12/2004 | Michelson |
| 6,514,256 B2 | 2/2003 | Zucherman et al. | 2004/0260397 A1 | 12/2004 | Lambrecht et al. |
| 6,520,991 B2 | 2/2003 | Huene | 2005/0010293 A1 | 1/2005 | Zucherman et al. |
| 6,554,833 B2 | 4/2003 | Levy | 2005/0049708 A1 | 3/2005 | Atkinson et al. |
| 6,565,570 B2 | 5/2003 | Sterett et al. | 2005/0075634 A1 * | 4/2005 | Zucherman et al. ........... 606/61 |
| 6,582,433 B2 | 6/2003 | Yun | 2005/0085814 A1 | 4/2005 | Sherman et al. |
| 6,582,467 B1 | 6/2003 | Teitelbaum et al. | 2005/0090824 A1 | 4/2005 | Shluzas et al. |
| 6,592,585 B2 | 7/2003 | Lee et al. | 2005/0113842 A1 | 5/2005 | Bertagnoli et al. |
| 6,602,260 B2 | 8/2003 | Harari et al. | 2005/0119665 A1 | 6/2005 | Keller |
| 6,610,065 B1 | 8/2003 | Branch et al. | 2005/0143827 A1 | 6/2005 | Globerman et al. |
| 6,626,944 B1 | 9/2003 | Taylor | 2005/0149035 A1 | 7/2005 | Pimenta et al. |
| 6,645,207 B2 | 11/2003 | Dixon et al. | 2005/0165398 A1 | 7/2005 | Reiley |
| 6,652,533 B2 | 11/2003 | O'Neil | 2005/0203512 A1 | 9/2005 | Hawkins et al. |
| 6,676,665 B2 | 1/2004 | Foley et al. | 2005/0203519 A1 | 9/2005 | Harms et al. |
| 6,685,742 B1 | 2/2004 | Jackson | 2005/0203624 A1 | 9/2005 | Serhan et al. |
| 6,695,842 B2 | 2/2004 | Zucherman et al. | 2005/0216002 A1 | 9/2005 | Simonson |
| 6,709,435 B2 | 3/2004 | Lin | 2005/0228391 A1 | 10/2005 | Levy et al. |
| 6,723,126 B1 | 4/2004 | Berry | 2005/0245937 A1 | 11/2005 | Winslow |
| 6,730,126 B2 | 5/2004 | Boehm, Jr. et al. | 2005/0261768 A1 | 11/2005 | Trieu |
| 6,733,534 B2 | 5/2004 | Sherman | 2005/0273166 A1 | 12/2005 | Sweeney |
| 6,736,818 B2 | 5/2004 | Perren et al. | 2005/0288672 A1 | 12/2005 | Feree |
| 6,743,257 B2 | 6/2004 | Castro | 2006/0004447 A1 | 1/2006 | Mastrorio et al. |
| 6,752,832 B2 | 6/2004 | Neumann | 2006/0004455 A1 | 1/2006 | Leonard et al. |
| 6,758,863 B2 | 7/2004 | Estes et al. | 2006/0015181 A1 | 1/2006 | Elberg |
| 6,761,720 B1 | 7/2004 | Senegas | 2006/0064165 A1 | 3/2006 | Zucherman et al. |
| 6,770,096 B2 | 8/2004 | Bolger et al. | 2006/0084983 A1 | 4/2006 | Kim |
| 6,783,530 B1 | 8/2004 | Levy | 2006/0084985 A1 | 4/2006 | Kim |
| 6,835,205 B2 | 12/2004 | Atkinson et al. | 2006/0084987 A1 | 4/2006 | Kim |
| 6,857,343 B1 | 2/2005 | Easterbrooks et al. | 2006/0084988 A1 | 4/2006 | Kim |
| 6,905,512 B2 | 6/2005 | Paes et al. | 2006/0085069 A1 | 4/2006 | Kim |
| 6,946,000 B2 | 9/2005 | Senegas et al. | 2006/0085070 A1 | 4/2006 | Kim |
| 6,981,975 B2 | 1/2006 | Michelson | 2006/0085074 A1 | 4/2006 | Raiszadeh |
| 7,011,685 B2 | 3/2006 | Arnin et al. | 2006/0089654 A1 | 4/2006 | Lins et al. |
| 7,041,136 B2 | 5/2006 | Goble et al. | 2006/0089719 A1 | 4/2006 | Trieu |
| 7,048,736 B2 | 5/2006 | Robinson et al. | 2006/0095136 A1 | 5/2006 | McLuen |
| 7,081,120 B2 | 7/2006 | Li et al. | 2006/0106381 A1 | 5/2006 | Ferree et al. |
| 7,087,083 B2 | 8/2006 | Pasquet et al. | 2006/0106397 A1 | 5/2006 | Lins |
| 7,097,648 B1 | 8/2006 | Globerman et al. | 2006/0111728 A1 | 5/2006 | Abdou |
| 7,097,654 B1 * | 8/2006 | Freedland .............. 606/232 | 2006/0116690 A1 | 6/2006 | Pagano |
| 7,101,375 B2 | 9/2006 | Zucherman et al. | 2006/0122620 A1 | 6/2006 | Kim |
| 7,163,558 B2 | 1/2007 | Senegas et al. | 2006/0129239 A1 | 6/2006 | Kwak |
| 7,189,234 B2 | 3/2007 | Zucherman et al. | 2006/0136060 A1 | 6/2006 | Taylor |
| 7,201,751 B2 | 4/2007 | Zucherman et al. | 2006/0182515 A1 * | 8/2006 | Panasik et al. ............. 411/346 |
| 7,217,293 B2 | 5/2007 | Branch, Jr. | 2006/0184247 A1 | 8/2006 | Edidin et al. |
| 7,238,204 B2 | 7/2007 | Le Couedic et al. | 2006/0184248 A1 | 8/2006 | Edidin et al. |
| 7,252,673 B2 | 8/2007 | Lim | 2006/0195102 A1 | 8/2006 | Malandain |
| 7,306,628 B2 | 12/2007 | Zucherman et al. | 2006/0217726 A1 | 9/2006 | Maxy et al. |
| 7,335,203 B2 | 2/2008 | Winslow et al. | 2006/0224159 A1 | 10/2006 | Anderson |
| 7,377,942 B2 | 5/2008 | Berry | 2006/0224241 A1 | 10/2006 | Butler et al. |
| 7,431,735 B2 | 10/2008 | Liu et al. | 2006/0235387 A1 | 10/2006 | Peterman |
| 7,442,208 B2 | 10/2008 | Mathieu et al. | 2006/0235532 A1 | 10/2006 | Meunier et al. |
| 7,445,637 B2 | 11/2008 | Taylor | 2006/0241601 A1 | 10/2006 | Trautwein et al. |
| 7,458,981 B2 | 12/2008 | Fielding et al. | 2006/0241613 A1 | 10/2006 | Brueneau et al. |
| 7,524,324 B2 | 4/2009 | Winslow et al. | 2006/0241757 A1 | 10/2006 | Anderson |
| 7,582,106 B2 | 9/2009 | Teitelbaum et al. | 2006/0247623 A1 | 11/2006 | Anderson et al. |
| 7,604,652 B2 | 10/2009 | Arnin et al. | 2006/0247640 A1 | 11/2006 | Blackwell et al. |
| 7,611,316 B2 * | 11/2009 | Panasik et al. ............. 411/346 | 2006/0264938 A1 | 11/2006 | Zucherman et al. |
| 7,621,950 B1 | 11/2009 | Globerman et al. | 2006/0271044 A1 | 11/2006 | Petrini et al. |
| 2001/0008600 A1 * | 7/2001 | Fraleigh .............. 411/252 | 2006/0271049 A1 | 11/2006 | Zucherman et al. |
| 2001/0016743 A1 | 8/2001 | Zucherman et al. | 2006/0271061 A1 | 11/2006 | Beyar et al. |
| 2002/0029039 A1 | 3/2002 | Zucherman et al. | 2006/0282079 A1 | 12/2006 | Labrom et al. |
| 2002/0082600 A1 | 6/2002 | Shaolian et al. | 2006/0293662 A1 | 12/2006 | Boyer, II et al. |
| 2002/0143331 A1 | 10/2002 | Zucherman et al. | 2006/0293663 A1 | 12/2006 | Walkenhorst et al. |
| 2002/0161368 A1 | 10/2002 | Foley et al. | 2007/0005064 A1 | 1/2007 | Anderson et al. |
| 2003/0040746 A1 | 2/2003 | Mitchell et al. | 2007/0010813 A1 * | 1/2007 | Zucherman et al. ........... 606/61 |
| 2003/0045940 A1 | 3/2003 | Eberlein et al. | 2007/0032790 A1 | 2/2007 | Aschmann et al. |
| 2003/0065330 A1 | 4/2003 | Zucherman et al. | 2007/0043362 A1 | 2/2007 | Malandain et al. |
| 2003/0153915 A1 | 8/2003 | Nekozuka et al. | 2007/0073289 A1 | 3/2007 | Kwak et al. |
| 2004/0010312 A1 | 1/2004 | Enayati | 2007/0100340 A1 | 5/2007 | Lange et al. |

| | | | |
|---|---|---|---|
| 2007/0112354 A1 | 5/2007 | Iwasaki et al. | |
| 2007/0123861 A1 | 5/2007 | Dewey et al. | |
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0270918 A1 | 10/2009 | Attias et al. | |
| 2010/0121379 A1 | 5/2010 | Edmond | |

FOREIGN PATENT DOCUMENTS

| | | |
|---|---|---|
| DE | 3922044 A1 | 2/1991 |
| DE | 4012622 C1 | 7/1991 |
| DE | 4217660 A1 | 12/1993 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Dispositivo Intervertebrale Ammortizzante DIAM," date unknown, p. 1.
"Tecnica Operatoria Per Il Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Ventures Inc., G. George., "You Can Hang Most Anything with Wall Anchors." Home Repair Articles, 2006, 11 pages, http://www.naturalhandyman.com/iip/inf/inffastener/infanchor/infanchor.shtm.

Sakowski, Michael., "Hanging Pictures on Drywall and Fastening in Drywall." DrywallInfo.com, 2005, 2 pages, http://www.drywallinfo.com/toggle.html.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

\* cited by examiner

INTERSPINOUS PROCESS DEVICES AND METHODS

BACKGROUND

The present application is directed to devices and methods for stabilizing vertebral members, and more particularly, to interspinous devices to engage onto the spinous processes and retain a predetermined distraction height.

Vertebral members comprise a body, pedicles, laminae, and processes. The body has an hourglass shape with a thinner middle section and wider ends, and include sections on the inferior and superior ends. Intervertebral discs are positioned between the bodies of adjacent vertebral members to permit flexion, extension, lateral bending, and rotation. The pedicles are two short rounded members that extend posteriorly from the body, and the laminae are two flattened members that extend medially from the pedicles. The processes are projections that serve as insertion points for the ligaments and tendons. The processes include the articular processes, transverse processes, and the spinous process. The spinous process is a single member that extends posteriorly from the junction of the two lamina. The spinous process may act as a lever to effect motion of the vertebral member.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

One method of correcting the damage is insertion of a device between the spinous processes. The device may reduce or eliminate the pain and neurological deficit, and increase the range of motion.

SUMMARY

The present application is directed to devices and methods for spacing and/or positioning spinous processes of vertebral members. The device may include a first wing to position on a first lateral side of spinous processes and a second wing to position on a second lateral side of spinous processes. An intermediate member may extend between the wings and fits within the interspinous space. The device may be selectively adjustable from a first orientation with the second wing received by the intermediate member. This first orientation may include a reduced sized to facilitate insertion of the device with a lateral approach into the interspinous space. The device may also be moved to a second orientation with the wing deployed from the intermediate member. The second orientation may provide for the second wing to be positioned on the second side of the spinous process opposite from the first wing. The intermediate member may be positioned within the interspinous space and contact the spinous processes to retain a predetermined distraction height.

DETAILED DESCRIPTION

The present application is directed to devices and methods for spacing and/or positioning spinous processes of vertebral members. The devices are selectively adjustable from a first orientation to a second orientation. The devices are inserted into the interspinous space while in the first orientation. After insertion, the devices are deployed to the second orientation to engage the spinous processes and retain a predetermined distraction height.

Figure 1:
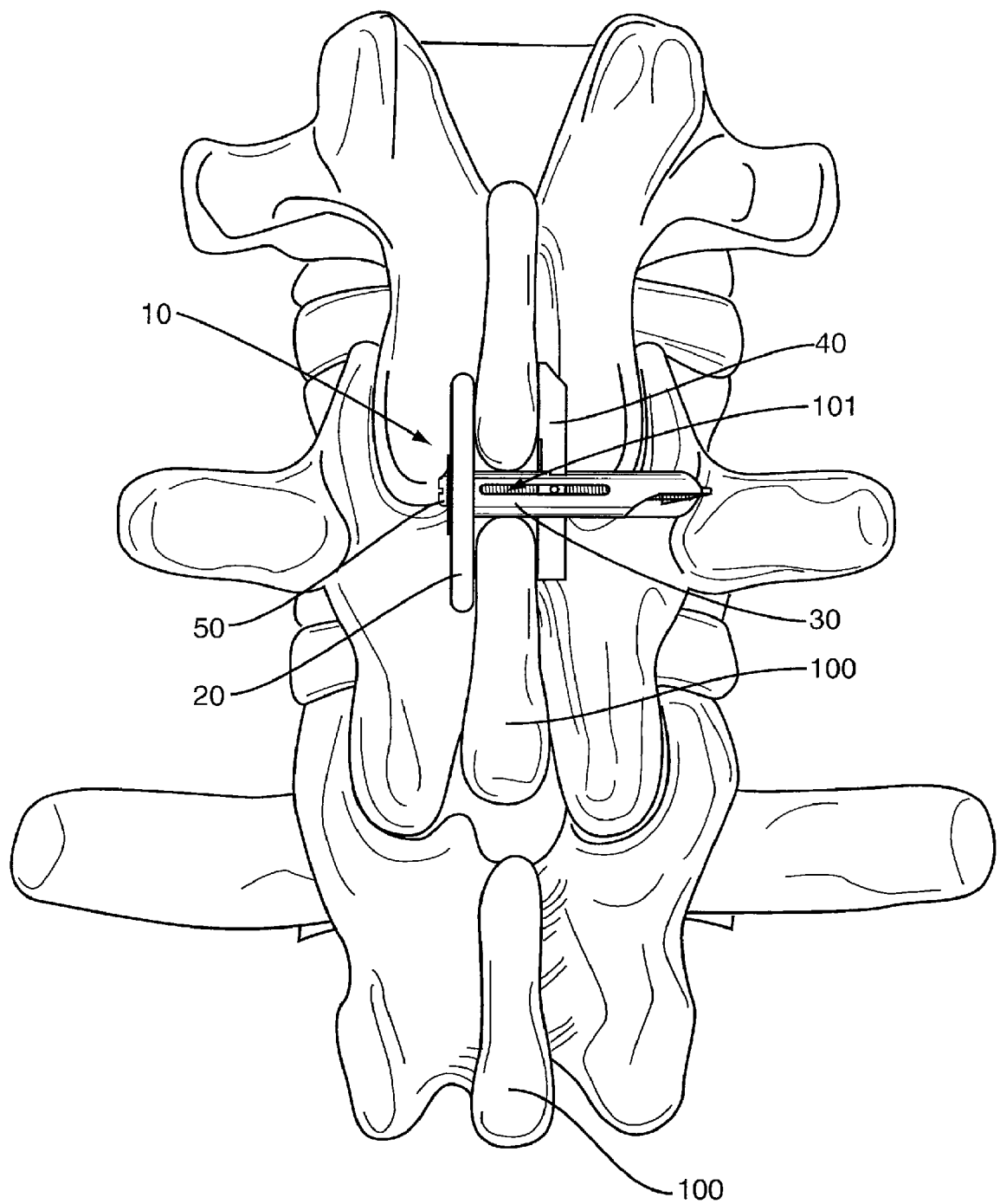
FIG. 1 is a schematic coronal view of a device attached to spinous processes according to one embodiment.

FIG. 1 illustrates one embodiment of the device 10 positioned within an interspinous space 101 formed between two spinous processes 100. FIG. 1 illustrates the device 10 in the second, deployed orientation. The device 10 includes a first wing 20 positioned on a first lateral side of the spinous processes 100, and a second wing 40 positioned on a second lateral side of the spinous processes 100. An intermediate member 30 is operatively attached to the wings 20, 40 and is positioned within the interspinous space 101. A driver 50 is inserted into the intermediate member 30 to deploy the second wing 40. The driver 50 may also be used to apply a compressive force to maintain the wings 20, 40 in engagement with the spinous processes 100.

Figure 2:
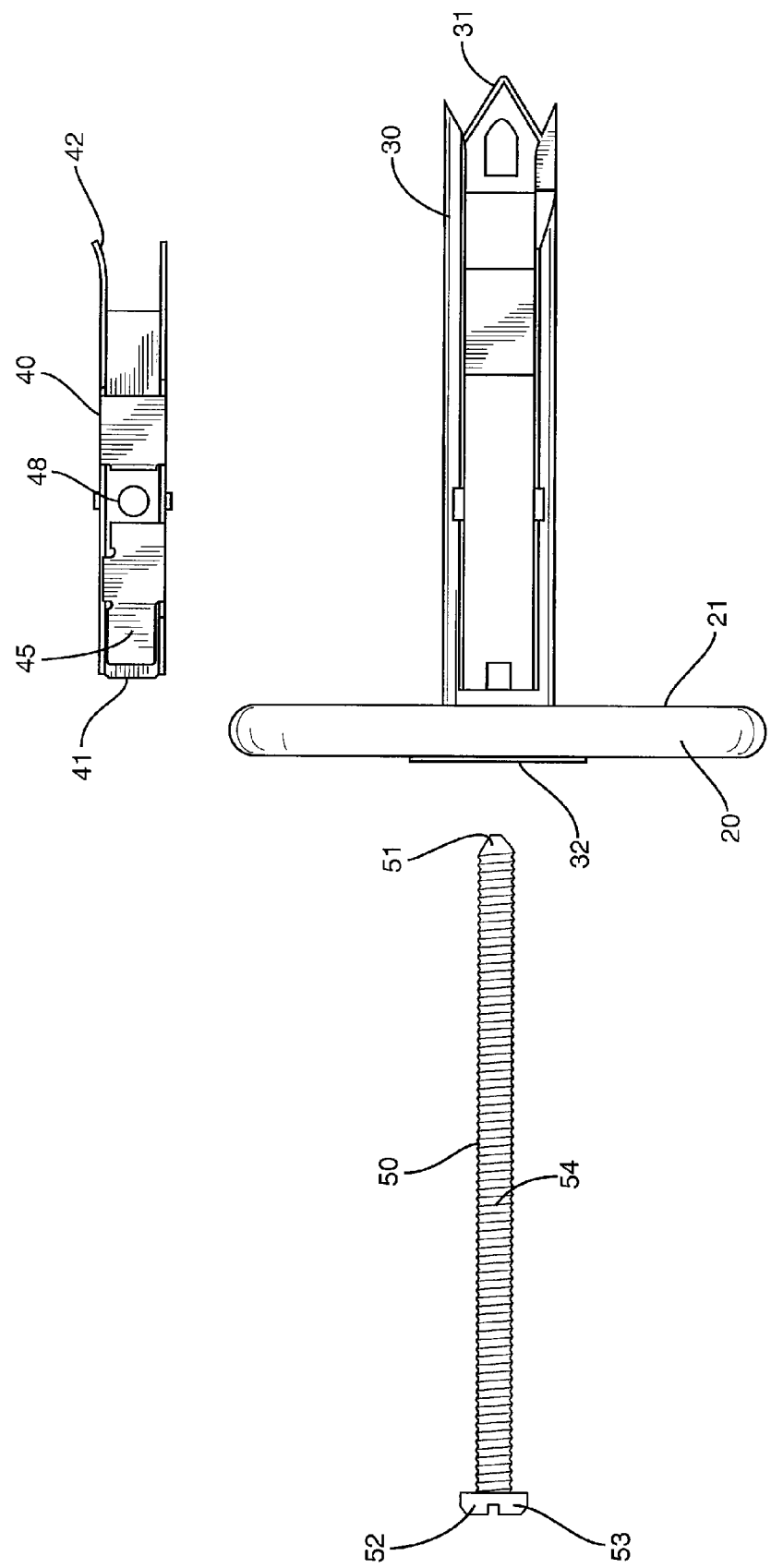
FIG. 2 is a top exploded view of the elements of a device according to one embodiment.

FIG. 2 illustrates an exploded view of a device 10 that includes wings 20, 40, intermediate member 30, and a driver 50. In this embodiment, the first wing 20 is integral with the intermediate member 30. First wing 20 and intermediate member 30 may be constructed as a single piece, or may be separate pieces that are attached together. Second wing 40 is pivotally attached to the intermediate member 30 as will be explained below. Driver 50 is sized to fit within the intermediate member 30 and deploy the second wing 40 from the first orientation to the second orientation.

First wing 20 includes an elongated shape to span across the width of the interspinous space 101 and contact the spinous processes 100. First wing 20 includes an inner side 21 that contacts the lateral sides of the spinous processes 100 as illustrated in FIG. 1. First wing 20 may be substantially straight, or may be curved depending upon the context of use. In one embodiment, the first wing 20 is centered on the intermediate member 30 with equal lengths extending above and below the member 30. In other embodiments, the lengths may be unequal. Teeth may be positioned on the inner side 21 to further engage the spinous processes.

Figure 3:
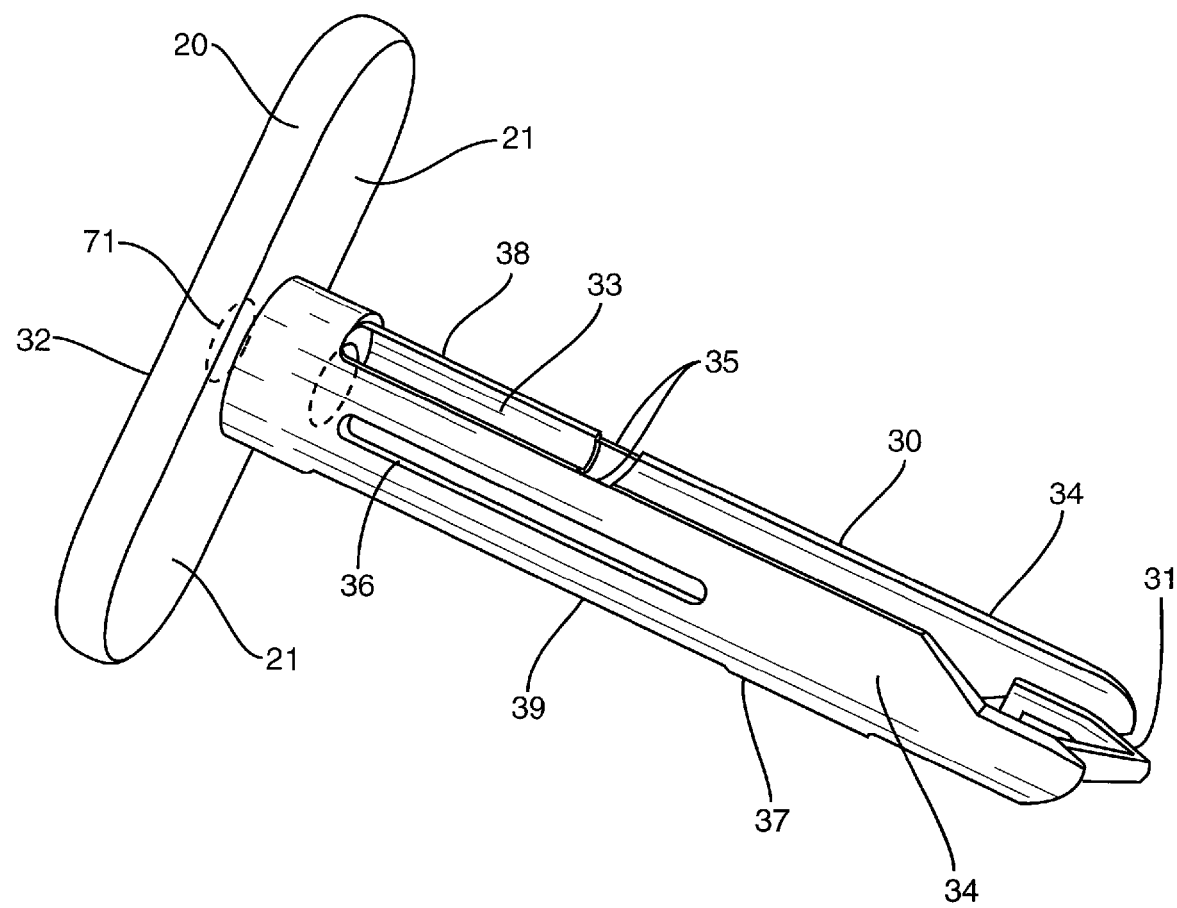
FIG. 3 is a perspective view of a first wing and an intermediate member according to one embodiment.

Intermediate member 30 is sized to fit within the interspinous space 101. As illustrated in FIG. 3, superior and inferior surfaces 38, 39 contact the spinous processes 100 and are spaced apart a distance to maintain a predetermined distraction height. The member 30 may loosely fit within the interspinous space, or may be sized for a more intimate, tighter fit. In one embodiment, a sleeve is inserted over the intermediate member 30 to increase the height and provide a tighter fit with the spinous processes 100. Intermediate member 30 further includes a first end 31 and a second opposing end 32. First end 31 may include a pointed configuration to facilitate insertion of the intermediate member 30 into the interspinous space 101. First end 31 may also include other shapes, including a bull-nose shape, bullet shape, or may be a general blunt shape. An interior section 33 is formed between opposing sidewalls 34. In one embodiment, interior section 33 is formed by opposing sidewalls 34 and a bottom wall 37 that forms the lower surface 39. In another embodiment, interior section 33 is formed just by sidewalls 34. In the various embodiments, sidewalls 34 and bottom wall 37 may be substantially solid, or may include one or more openings. In one embodiment, bottom wall 37 is a single shortened strip extending between sidewalls 34 with the remainder of the bottom being substantially open.

The interior section 33 is sized to receive the second wing 40. One or more notches 35 may be positioned on the inner sides of the sidewalls 34. Notches 35 may lead inward from one of the superior and inferior surfaces 38, 39 and terminate at one or more slots 36 cut along the sidewall 34. The notches 35 and slots 36 are configured to position the second wing 40 as will be explained below. Second end 32 may include an opening 71 that leads into the interior section 33 and is sized to receive the driver 50. In one embodiment, opening 71 is threaded.

Figure 4:
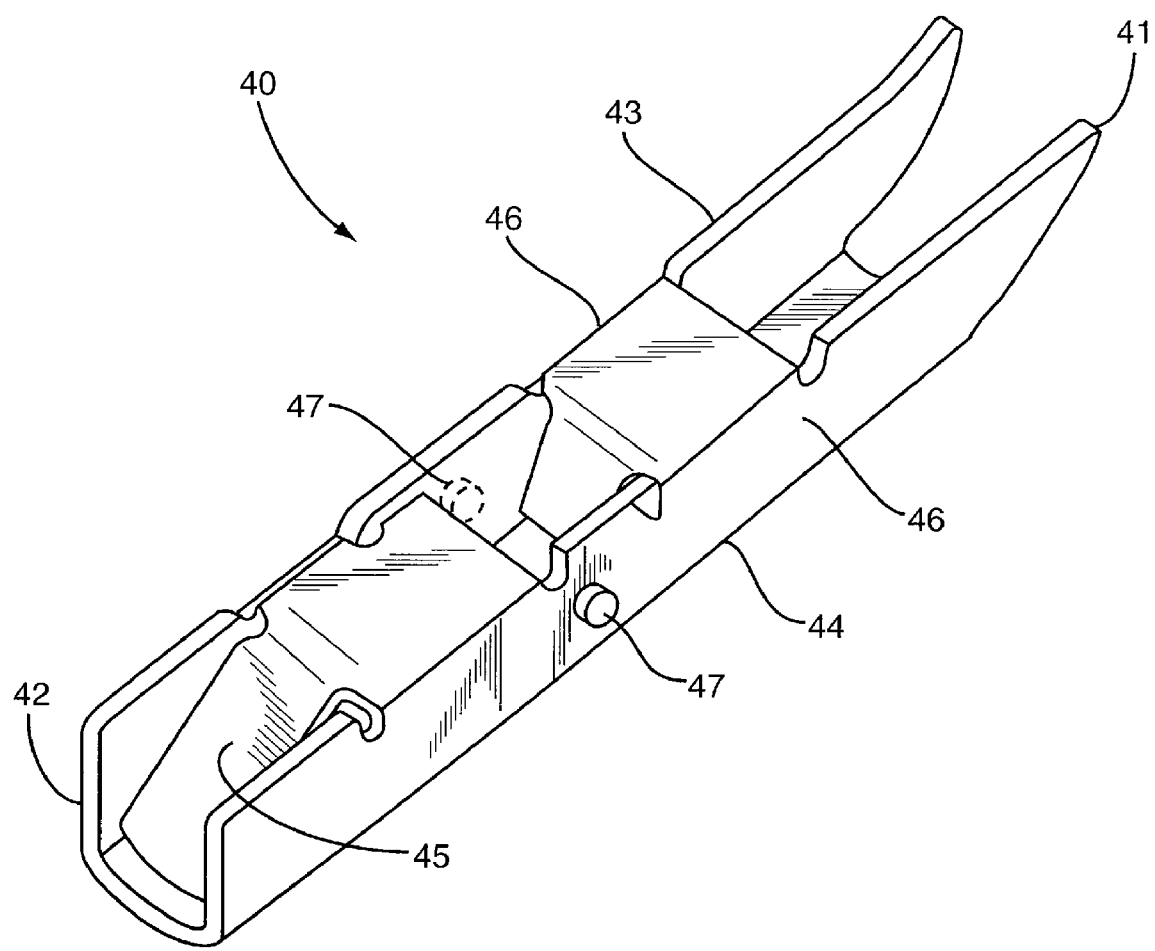
FIG. 4 is a perspective view of a second wing according to one embodiment.

Second wing 40 is pivotally attached to the intermediate member 30. As illustrated in FIG. 4, second wing 40 includes a first end 41 and a second end 42. Second wing 40 may further include opposing sidewalls 46 that form first and second sides 43, 44. A ramped section 45 may be positioned towards the second end 42. In the embodiment of FIG. 4, ramped section 45 ramps upward from the second side 44 towards the first side 43. In another embodiment, ramped section 45 ramps from the first side 43 towards the second side 44. The ramped section 45 may extend the entirety between the first and second sides 43, 44, or just a portion of the distance. An opening 48 (FIG. 2) extends through the second wing 40. In one embodiment, the opening 48 is positioned between the ramped section 45 and the first end 41. Opening 48 may be threaded to receive the driver 50.

Second wing 40 may also include one or more extensions 47 that extend outward from the sidewalls 46 as illustrated in FIG. 4. Extensions 47 are sized to fit within the notches 35 and slots 36 of the intermediate member 30 to connect and position the second wing 40 to the intermediate member 30.

Figure 5:
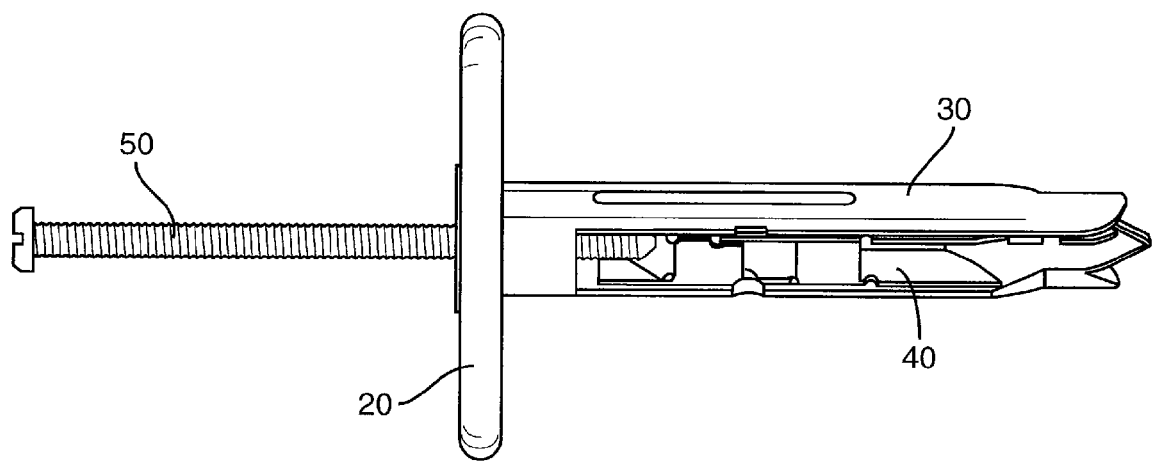
FIG. 5 is a perspective view of a device in a first orientation according to one embodiment.

FIG. 5 illustrates the second wing 40 received by the interior section 33 of the intermediate member 30. In one embodiment of the first orientation, second wing 40 fits within the interior section 33 with the first side 43 being flush with or recessed below the superior surface 38 of the intermediate member 30 and the second side 44 being flush or recessed below the inferior surface 39. In the first orientation, the second wing 40 is substantially aligned with the intermediate member 30 and may be substantially parallel with the intermediate member 30. In one embodiment of the first orientation, the second wing 40 is substantially perpendicular with the first wing 20. The length of the second wing 40 measured between the first and second ends 41, 42 may be less than the length of the interior section 33. In another embodiment, the length of the second wing 40 is greater than the interior section 33 with the first end 41 extending outward beyond the intermediate member 30.

Driver 50 is sized to fit within the intermediate member 30 and deploy the second wing 40. As illustrated in FIG. 2, driver 50 includes an elongated shape with a first end 51 and second end 52. The driver 50 contacts the second wing 40 causing a pivoting action of the second wing 40 relative to the intermediate member 30. In one embodiment, first end 51 includes a tip that contacts the second wing 40. In another embodiment, an intermediate section of the driver 50 between the ends 51, 52 contacts the second wing 40. Second end 52 may include a head 53 with an enlarged width. Head 53 may include a receptacle such as but not limited to a Torx, Allen, Philips receptacle to mate with a driving tool and rotate the driver 50. Threads 54 may extend along a section or the entirety of the driver 50.

Figure 6A:
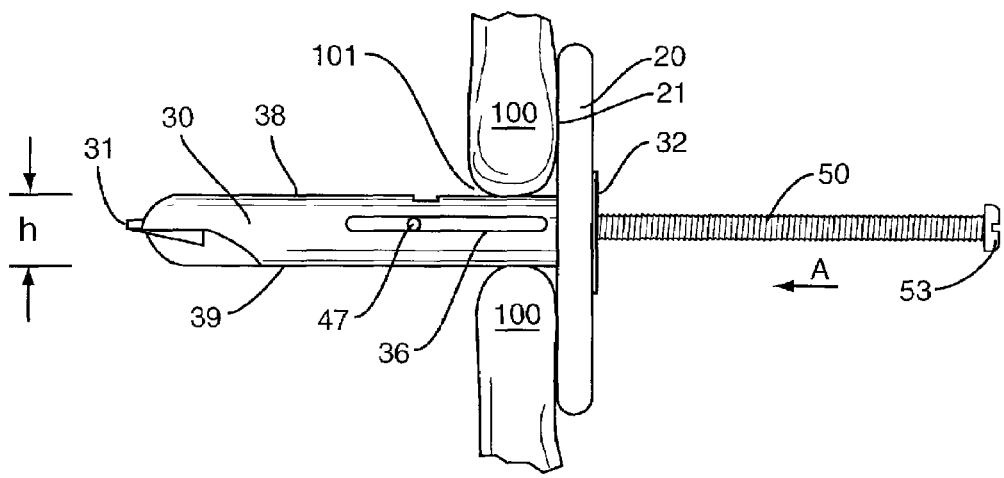
FIG. 6A is a side view of a device in a first orientation according to one embodiment.
Figure 6B:
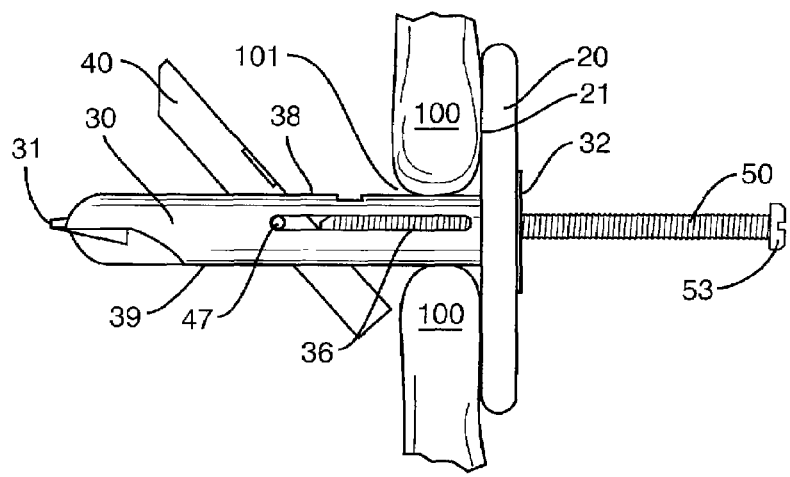
FIG. 6B is a side view of a device in an intermediate orientation according to one embodiment.
Figure 6C:
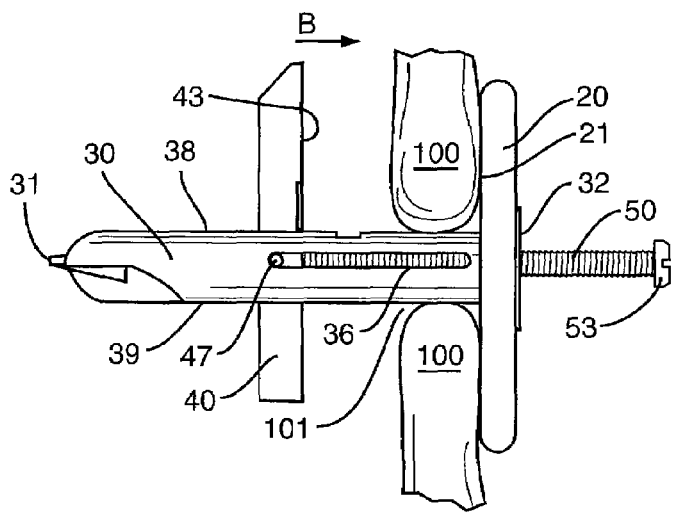
FIG. 6C is a side view of a device in a second orientation according to one embodiment.

FIGS. 6A-6C illustrate one embodiment of the device being deployed from the first orientation to the second orientation. FIG. 6A illustrates the device 10 in the first orientation with the second wing 40 received by the intermediate member 30. In this embodiment, second wing 40 is positioned within the interior section 33 of the intermediate member 30 and the height h is defined between the superior and inferior surfaces 38, 39 of the intermediate member 30.

The first orientation provides for inserting the device 10 into the patient. The shape provides for insertion through a lateral approach in the direction illustrated by arrow A with the first end 31 of the intermediate member 30 inserted first into the interspinous space 101. A lateral approach may be beneficial because it preserves the supraspinous and interspinous ligaments. The height h provides for the intermediate member 30 and second wing 40 to fit within the interspinous space 101. Full insertion may occur when the first side 21 of the first wing 20 contacts the first lateral side of the spinous processes 100 as illustrated in FIG. 6A. In another embodiment, full insertion occurs with the first side 21 spaced away from the spinous processes 100. In one embodiment, driver 50 is inserted into the intermediate member 30 during insertion of the device 10 into the interspinous space 101. In another embodiment, driver 50 is inserted after the device 10 is inserted into the interspinous space 101.

In the first orientation, the second wing 40 is received by the intermediate member 30. The ramped section 45 faces towards the second end 32 of the intermediate member 30. In one embodiment, extensions 47 that extend outward from the sidewalls 46 of the second wing 40 are positioned within slots 36 that extend along the sidewalls 34 of the intermediate member 30. The extensions 47 may slide within the slots 36 to laterally move the second wing 40 relative to the intermediate member 30. In another embodiment, the second wing 40 is laterally fixed relative to the intermediate member 30.

FIG. 6B illustrates the device 10 in an intermediate orientation with the second wing 40 partially deployed from the intermediate member 30. Deployment is caused by insertion of the driver 50 into the intermediate member 30 and contact with the second wing 40. In one embodiment, a tip of the driver 50 contacts the ramped section 45 of the second wing 40. Continued insertion of the driver 50 into the intermediate member 30 causes additional pivoting motion of the second wing 40 as the tip of the driver 50 slides along the ramped section 45. Contact of the driver 50 may also cause the second wing 40 to laterally slide along the intermediate member 30. This sliding motion causes an increase in distance between the first wing 20 and the second wing 40. The sliding motion may also facilitate positioning of the second wing 40 on the second lateral side of the spinous processes 100 opposite from the first wing 20.

FIG. 6C illustrates the device 10 in the second orientation with the second wing 40 pivoted relative to the intermediate member 30. In one embodiment, the second wing 40 is substantially perpendicular to the intermediate member 30 in the second orientation. The second wing 40 may be substantially parallel with the first wing 20. Insertion of the driver 50 may cause the first end 51 to slide along the second wing 40 and into the opening 48 in the second wing 40. Continued insertion causes the driver 50 to be inserted through the opening 48 thereby connecting the driver 50 to the second wing 40. Continued insertion of the driver 50 into the second wing 40 causes the second wing 40 to move laterally in the direction indicated by arrow B. This provides for the second wing 40 to laterally move and the first side 43 to contact the second lateral side of the spinous processes 100 opposite from the first wing 20. This force maintains the device 10 attached to the spinous processes 100. Teeth may be positioned on the first side 43 to further engage the spinous processes 100. In another embodiment, the second wing 40 remains spaced away from the second lateral side.

As illustrated in FIG. 6C, the height of the intermediate member 30 is sized to fit within the interspinous space 101. The inferior sides 38, 39 contact the spinous processes 100 and the height between the sides 38, 39 is sized to maintain the spinous processes 100 at a predetermined retraction height.

Figure 7:
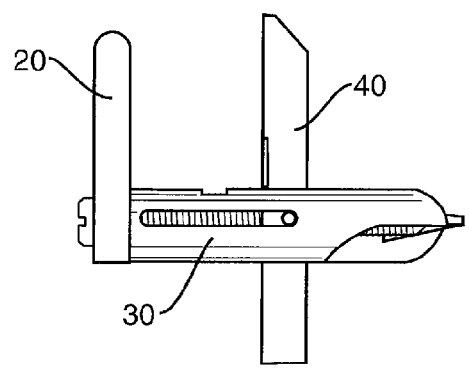
FIG. 7 is a schematic side view of a device according to one embodiment.

Wings 20, 40 may include a variety of different shapes and sizes. In one embodiment as illustrated in FIGS. 6A-C, wings 20, 40 include substantially the same length and extend outward from the intermediate member 30 in substantially the same directions. In another embodiment, one of the wings 20, 40 is a different size. FIG. 7 illustrates an embodiment with wing 40 including a greater size. Wing 40 extends outward from the intermediate member 30 in opposing directions. In one embodiment, one or both wings 20, 40 include an anatomical shape to match the contours of the spinous processes 100.

In one embodiment, wings 20, 40 may extend outward from opposing sides of the intermediate member 30 such as the embodiment illustrated in FIGS. 1 and 6C. In another embodiment, wings 20, 40 extend outward from a single side of the intermediate member 30. Wing 20 in FIG. 7 illustrates an embodiment that extends outward in a single direction.

Figure 8:
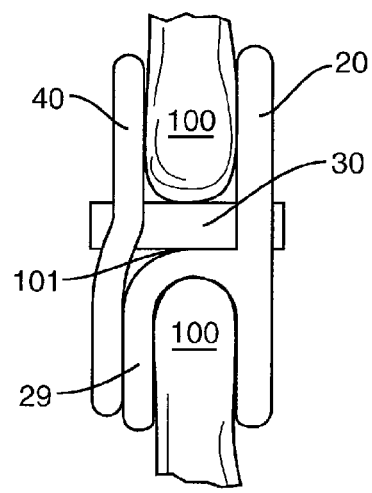
FIG. 8 is a schematic side view of a device according to one embodiment.

FIG. 8 illustrates another embodiment with the first wing 20 including an extension 29 that extends around the side of the spinous process 100. The first wing 20 includes a substantially "h" shape. The intermediate member 30 fits within the interspinous space 101 and attaches with the second wing 40 as in the other embodiments.

The spinous processes 100 may be accessed from various approaches, including a lateral, posterior, posterior-lateral, and oblique. The approaches may be made through various incisions, including a midline incision, a mini-open incision, and a paramedial incision. The devices 10 and methods may be used on various regions of the spine, including the cervical, thoracic, lumbar and/or sacral regions.

Figure 9:
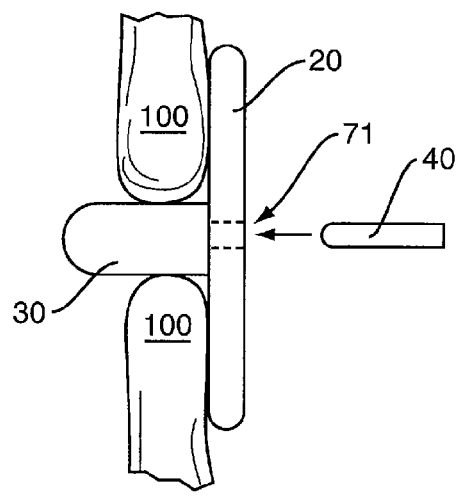
FIG. 9 is a side view of a device in a first orientation according to one embodiment.

In one embodiment as illustrated in FIGS. 6A-6C, the second wing 40 is positioned in the intermediate member 30 when the device 10 is initially inserted into the patient. In another embodiment as illustrated in FIG. 9, the second wing 40 is a separate member that is initially removed from the intermediate member 30. The second wing 40 is inserted through the opening 71 in the intermediate member 30 after the intermediate member 30 and first wing 20 are inserted into the patient. The second wing 40 is sized to fit within the opening 71 and move laterally through the interspinous space 101 and be deployed in a manner similar to the method described in FIGS. 6B and 6C.

The wings 20, 40 and intermediate member 30 may be constructed of a variety of materials. Examples of the materials include but are not limited to plastics, titanium, titanium alloys such as nickel-titanium, stainless steel, PEEK, PEEK-carbon composites, polyimide, polyetherimide, polyurethane, ceramics, and silicon. In one embodiment, one or more of the elements 20, 30, 40 are constructed of a first material and then coated with a second material. In one embodiment, the coating includes an osteo-conductive material to induce bone growth, such as hydroxyapatite and BMP. In one embodiment, a polyester mesh may be wrapped around one or more of the elements. In one embodiment, sections of the elements are coated with a second material. In one specific embodiment, the ramped section 45 is coated with a rigid material to prevent wear due to contact with the driver end 51. In another specific embodiment, opening 48 in the second wing 40 is coated with a rigid material to prevent wear due to mating contact with the driver 50.

In one embodiment, two or more of elements 20, 30, 40 are molded together. In one specific embodiment, intermediate member 30 is molded to second wing 40.

In one embodiment as illustrated in FIG. 5, the second wing 40 nests within the intermediate member 30. Second wing 40 may also be positioned on an exterior of the intermediate member 30 when the device 10 is in the first orientation.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment with the second wing 40 in a first orientation positioned within the intermediate member 30, the second wing 40 extends outward an amount from the interior section 33. The present embodiments are, therefore, to be considered in all respects as illustrative and not restrictive, and all changes coming within the meaning and equivalency range of the appended claims are intended to be embraced therein.

What is claimed is:

1. A device for use in an interspinous space formed between spinous processes of first and second vertebral members, the device comprising:
   a first wing sized to contact a first lateral side of the first and second vertebral members, the first wing having an elongated shape with a major axis and a minor axis, the major axis being longer than the minor axis, the first wing having an inner surface that bears against lateral surfaces of the spinous processes;
   an intermediate member defined by a pair of sidewalls, an open bottom portion and an open top portion, the intermediate member extending outward from the first wing and sized to fit within the interspinous space between the first and second vertebral members and space apart the spinous processes, wherein the open bottom portion and the open top portion are substantially aligned with the major axis of the first wing;
   a second wing pivotally attached to the intermediate member and pivotable between a first orientation that is substantially aligned with the intermediate member to be inserted through the interspinous space and a second orientation that is substantially transverse to the intermediate member and passes through the open bottom portion and the open top portion and extends outward from beyond the sidewalls of the intermediate member to contact a second lateral side of the first and second vertebral members, the second wing including a greater height relative to the interspinous space in the second orientation than in the first orientation; and the second wing including the same shape and size in both the first and second orientations.

2. The device of claim 1, wherein the first wing extends outward from the intermediate member in opposing directions and the first wing is substantially perpendicular to the intermediate member.

3. The device of claim 1, wherein the second wing is substantially parallel to the intermediate member in the first orientation.

4. The device of claim 1, wherein the first wing is fixedly positioned to the intermediate member.

5. The device of claim 1, wherein the second wing is positioned within the intermediate member in the first orientation.

6. The device of claim 1, wherein the second wing includes a ramped section that faces towards a second end of the intermediate member when the second wing is in the first orientation.

7. The device of claim 6, wherein the second wing further includes an opening positioned on an opposite side of the ramped section from the second end of the intermediate member when the second wing is in the first orientation.

8. The device of claim 1, further including a driver that extends into the intermediate member and through the second wing when the second wing is in the second orientation.

9. The device of claim 1, further comprising a coating placed on at least one of the first wing, second wing, and intermediate member.

10. The device of claim 1, further including a sleeve disposed around the intermediate member to increase a size of the intermediate member.

11. The device of claim 1, wherein the second wing includes extensions that extend outward from sidewalls and engage within slots in the intermediate member.

12. A device for use in an interspinous space formed between spinous processes of first and second vertebral members, the device comprising:

a first wing having a major axis and an inner surface that is sized to contact a first lateral side of the first and second vertebral members;

an intermediate member extending outward from the first wing and including superior and inferior sides positioned a predetermined distance apart to contact and space the spinous processes, the superior and inferior sides including openings, the intermediate member also including intermediate sides between the superior and inferior sides; and a second wing including an elongated shape that extends between first and second ends and is pivotally attached to the intermediate member and pivotable between a first orientation that is substantially perpendicular to the first wing to be inserted through the interspinous space and a second orientation that extends through each of the openings and is substantially parallel to the major axis of the first wing to contact a second lateral side of the first and second vertebral members;

the first and second ends being positioned the same distance apart from each other in both the first and second orientations;

the first wing extending outward a greater distance on the superior and inferior sides of the intermediate member than on the intermediate sides to extend along and contact the spinous processes away from the interspinous space.

13. The device of claim 12, wherein the intermediate member includes a hollow interior section to receive the second wing in the first orientation.

14. The device of claim 13, wherein the second wing is contained within the hollow interior section in the first orientation.

15. The device of claim 12, wherein at least one of the first wing, second wing, and intermediate member are coated with a second material.

16. A method of positioning a spacer within an interspinous space formed between spinous processes of first and second vertebral members, the method comprising:

inserting an intermediate member of the spacer into the interspinous space and spacing apart the spinous processes, the intermediate member having a superior opening and an inferior opening;

positioning an elongated first wing having a major axis and a minor axis, wherein the first wing is attached to the intermediate member, at a first lateral side of the spinous processes of the first and second vertebral members such that the major axis extends along at least a portion of both the first and second vertebral members; and pivoting an elongated second wing that has first and second opposing ends and that is pivotably attached to the intermediate member from a first orientation substantially aligned with the intermediate member to a second orientation transverse to the intermediate member and extending through the superior opening and the inferior opening along a second lateral side of the spinous processes of the first and second vertebral members and generally aligned with the major axis of the first wing without changing a shape of the second wing, the first and second opposing ends of the second wing being spaced apart a same distance in each of the first and second orientations.

17. The method of claim 16, wherein the step of pivoting the second wing from the first orientation substantially aligned with the intermediate member to the second orientation transverse to the intermediate member further comprises pivoting the second wing from an interior section of the intermediate member.

18. The method of claim 16, further comprising reducing a distance between the first and second wings and applying a compressive force to the spinous processes.

19. The method of claim 16, further comprising sliding the second wing along slots in the intermediate member while pivoting the second wing from the first orientation to the second orientation.

* * * * *